United States Patent
Kopchick et al.

(10) Patent No.: US 11,426,445 B2
(45) Date of Patent: Aug. 30, 2022

(54) METHODS FOR TREATING CANCERS USING FAT SPECIFIC PROTEIN 27 (FSP27) COMPOSITIONS

(71) Applicant: Ohio University, Athens, OH (US)

(72) Inventors: John Kopchick, Athens, OH (US); Vishwajeet Puri, Athens, OH (US); Vishva Sharma, Athens, OH (US); Reetobrata Basu, Athens, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 16/646,009

(22) PCT Filed: Sep. 17, 2018

(86) PCT No.: PCT/US2018/051309
§ 371 (c)(1),
(2) Date: Mar. 10, 2020

(87) PCT Pub. No.: WO2019/060245
PCT Pub. Date: Mar. 28, 2019

(65) Prior Publication Data
US 2020/0222502 A1    Jul. 16, 2020

Related U.S. Application Data

(60) Provisional application No. 62/560,326, filed on Sep. 19, 2017.

(51) Int. Cl.
*A61K 38/17* (2006.01)
*A61P 31/00* (2006.01)
*A61P 35/00* (2006.01)

(52) U.S. Cl.
CPC .......... *A61K 38/1761* (2013.01); *A61P 31/00* (2018.01); *A61P 35/00* (2018.01)

(58) Field of Classification Search
None
See application file for complete search history.

(56) References Cited

U.S. PATENT DOCUMENTS

| | | |
|---|---|---|
| 2003/0124113 A1 | 7/2003 | Hillman et al. |
| 2006/0160133 A1 | 7/2006 | Czech et al. |
| 2009/0215895 A1* | 8/2009 | Ferrante .......... A61P 3/04 514/560 |
| 2014/0206543 A1 | 7/2014 | Rogan et al. |

FOREIGN PATENT DOCUMENTS

| | | | |
|---|---|---|---|
| CN | 1388132 A | * | 1/2003 |
| WO | WO2016069854 A1 | | 5/2016 |
| WO | WO2016175913 A1 | | 11/2016 |

OTHER PUBLICATIONS

Machine translation of CN-1388132.*
Yampolsky, Lev Y. and Stoltzfus, Arlin; "The exchangeability of amino acids in proteins." Genetics (2005) 170 p1459-1472.*
United States Patent and Trademark Office International Search Report and Written Opinion for PCT application No. PCT/US2018/051309, dated Feb. 25, 2019, p. 1-18.
Liang et al. "Molecular cloning and characterization of CIDE-3, a novel member of the cell-death-inducing DNA-fragmentation-factor (DFF45)-like effector family," Biochem. J., 2003, p. 195-203, vol. 370, Biochemical Society.
Puri et al. "Cidea is associated with lipid droplets and insulin sensitivity in humans," PNAS, 2008, p. 7833-7838, vol. 105 No. 22, Proceedings of the National Academy of Sciences of the United States of America.
Min et al. "CIDE-3 interacts with lipopolysaccharide-induced tumor necrosis factor, and overexpression increases apoptosis in hepatocellular carcinoma," Medical Oncology, 2011, p. 219-227, vol. 28, Supp. 1, Springer US, abstract only.
Puri et al. "Fat specific Protein 27, a Novel Lipid Droplet Protein That Enhances Triglyceride Storage," The Journal of Biological Chemistry, 2007, p. 34213-34218, vol. 282 No. 47, the American Society for Biochemistry and Molecular Biology, Inc.
Jambunathan et al. "FSP27 Promotes Lipid Droplet Clustering and Then Fusion to Regulate Triglyceride Accumulation," PLoS ONE, 2011, p. 1-12, vol. 6 Issue 12, PLOS.

* cited by examiner

*Primary Examiner* — Fred H Reynolds
(74) *Attorney, Agent, or Firm* — MacMillan, Sobanski & Todd, LLC

(57) ABSTRACT

FSP27 compositions and methods for treating cancers are described.

4 Claims, 13 Drawing Sheets
(3 of 13 Drawing Sheet(s) Filed in Color)
Specification includes a Sequence Listing.

E

FSP27 (120-239)

FSP27 (120-220)

FSP27 (120-210)

FSP27 (140-210)

Functional domains of FSP27

Table 1

| SEQ ID | CF # | Amino acid positions | Peptide length | Peptide Sequence |
|---|---|---|---|---|
| 1 | CF1 | aa 1-60 | 60 | MEYAMKSLSLLYPKSLSRHVSVRTSVVTQQLLSEPSPKAPRARPCRVSTADRSVRKGIMA |
| 2 | CF2 | aa 173-220 | 48 | YDLHCCGAKRIMKEAFRWALFSMQATGHVLLGTSCYLQQLLDATEEGQ |
| 3 | CF3 | aa 40-120 | 81 | PRARPCRVSTADRSVRKGIMAYSLEDLLLKVRDTLMLADKPFFLVLEEDGTTVETEEYFQALAGDTVFMVLQKGQKWQPPS |
| 4 | CF4 | aa 120-140 | 21 | SEQGTRHPLSLSHKPAKKIDV |
| 5 | CF5 | aa 210-220 | 11 | QQLLDATEEGQ |
| 6 | CF6 | aa 210-239 | 29 | QQLLDATEEGQPPKGKASSLIPTCLKILQ |
| 7 | CF7 | aa 120-239 | 120 | SEQGTRHPLSLSHKPAKKIDVARVTFDLYKLNPQDFIGCLNVKATFYDTYSLSYDLHCCGAKRIMKEAFRWALFSMQATGHVLLGTSCYLQQLLDATEEGQPPKGKASSLIPTCLKILQ |
| 8 | CF8 | aa 120-130 | 11 | SEQGTRHPLSL |
| 9 | CF9 | aa 120-210 | 91 | SEQGTRHPLSLSHKPAKKIDVARVTFDLYKLNPQDFIGCLNVKATFYDTYSLSYDLHCCGAKRIMKEAFRWALFSMQATGHVLLGTSCYLQ |
| 10 | CF10 | aa 120-220 | 101 | SEQGTRHPLSLSHKPAKKIDVARVTFDLYKLNPQDFIGCLNVKATFYDTYSLSYDLHCCGAKRIMKEAFRWALFSMQATGHVLLGTSCYLQQLLDATEEGQ |
| 11 | CF11 | aa 140-210 | 71 | VARVTFDLYKLNPQDFIGCLNVKATFYDTYSLSYDLHCCGAKRIMKEAFRWALFSMQATGHVLLGTSCYLQ |
| 12 | CF12 | Aa 1-238 | 238 | MEYAMKSLSLLYPKSLSRHVSVRTSVVTQQLLSEPSPKAPRARPCRVSTADRSVRKGIMAYSLEDLLLKVRDTLMLADKPFFLVLEEDGTTVETEEYFQALAGDTVFMVLQKGQKWQPPSEQGTRHPLSLSHKPAKKIDVARVTFDLYKLNPQDFIGCLNVKATFYDTYSLSYDLHCCGAKRIMKEAFRWALFSMQATGHVLLGTSCYLQQLLDATEEGQPPKGKASSLIPTCLKILQ |

FIG. 15

METHODS FOR TREATING CANCERS USING FAT SPECIFIC PROTEIN 27 (FSP27) COMPOSITIONS

CROSS-REFERENCE TO RELATED APPLICATIONS

This application is a national stage application filed under 35 U.S.C. § 371 of international application PCT/US2018/051309, filed under the authority of the Patent Cooperation Treaty on Sep. 17, 2018, which claims the priority to United States Provisional Application Ser. No. 62/560,326 filed Sep. 19, 2017, the entire disclosures of which are expressly incorporated herein by reference.

SEQUENCE LISTING

The instant application contains a Sequence Listing which has been submitted via EFS-web and is hereby incorporated by reference in its entirety. The ASCII copy, created on Aug. 28, 2018, is named 3834_59497-PCT_SEQLIST_OU-18001_SL.txt.txt, and is 19,892 bytes in size.

BACKGROUND OF THE INVENTION

Human cancers of liver, pancreas, and kidney together account for millions of cancer cases and deaths in United States alone every year. All three cancer types are known to be highly resistant to currently known chemotherapy and targeted therapies. Also, these cancers are highly metastatic, and recurrent in nature with very low five-year survival rates of 3%, 2%, and 8% for liver, pancreas and kidney cancers, respectively.

The lack of therapeutic options and increasing resistance to available drugs, creates a huge challenge in cancer therapy. Additionally, the high doses of chemotherapy required at advanced stage causes significant adverse side-effects, deteriorating the quality of life of the patients.

There is a great need for life-saving treatments for the millions of patients suffering from cancers.

There is no admission that the background art disclosed in this section legally constitutes prior art.

SUMMARY OF THE INVENTION

Fat Specific Protein (FSP27), also known as cell death-inducing DFFA-like effector c (CIDEC in humans and Cidec in mice; also abbreviated Cide-c or Cide-3) is a member of the cell death-inducing DNA fragmentation factor-like effector family—a group of genes that play an important role in apoptosis. FSP27 promotes lipid droplet formation in adipocytes and may mediate adipocyte apoptosis. Its function is regulated by insulin. The invention described herein identifies an additional, novel role of FSP27 as a therapeutic target for treating cancer.

In a first broad aspect, described herein are uses of FSP27 compositions. It is now described herein that the exogenous delivery of FSP27 would be able to rescue FSP27 dysfunction or augment the endogenous function of FSP27.

In another broad aspect, described herein are methods of treatment where administering exogenous recombinant FSP27 (rFSP27) as a therapeutic for the treatment of human cancers including but not limited to liver, pancreas, kidney, melanoma, breast, prostate lung, colon and gastric cancers.

Such uses include, but are not limited to, increasing levels of FSP27 in a subject by administering exogenous recombinant FSP27 (rFSP27).

In certain embodiments, one fragment of FSP27, namely amino acids 120-140, inhibits the growth of several types of human cancers.

Described herein are examples showing the anti-cancer activity of exogenously administered human FSP27 and peptide fragments or analogs in human cancers.

Recombinant FSP27 sensitizes melanoma and liver, pancreatic and kidney cancer cells that can then be killed by a very low dose of prescribed chemotherapeutic agents.

Chemotherapy drugs cause adverse side effects but use of recombinant FS27 in combination with significantly lower doses of the chemotherapeutic agents acts to significantly reduce these side effects.

In another broad aspect, described herein are pharmaceutical compositions comprising one or more FSP27 medicaments. FSP27 medicaments may be administered as a pharmaceutically acceptable salt, or as a pegylated composition, or be modified in a pharmaceutically acceptable manner so as to improve the therapeutic properties. FSP27 medicaments may also be administered optionally together with one or more inert carriers and/or diluents.

The FSP27 medicament is present in an amount sufficient to treat one or more types of cancer.

In another broad aspect, described herein is a method of treating a subject, the method comprising: administering a composition comprising a nucleic acid encoding a FSP27 protein or a fragment thereto a subject; wherein, the FSP27 protein has an amino acid sequence having greater than 85% homology to at least one of the FSP27 sequences shown in FIG. 14; or the FSP27 fragments shown in FIG. 15.

In certain embodiments, the FSP27 protein has an amino acid sequence having greater than about 90% homology to the FSP27 sequences.

In certain embodiments, the FSP27 protein has an amino acid sequence having greater than about 95% homology to the FSP27 sequences.

In certain embodiments, the FSP27 protein has an amino acid sequence having greater than about 99% homology to the FSP27 sequences.

In certain embodiments, the FSP27 protein is naturally occurring.

In certain embodiments, the FSP27 protein is a recombinant protein.

In certain embodiments, the FSP27 protein comprises a core FSP27 domain, such as amino acids comprising: aa120-239 of FSP27; aa120-230 of FSP27; aa120-210; aa120-140; aa120-220; aa140-210; and/or aa173-220 of FSP27.

In certain embodiments, the subject is a human.

In certain embodiments, the subject experiences reduced cancer cell viability.

In certain embodiments, the nucleic acid encoding the FSP27 protein is operably linked to a constitutive transcriptional regulatory sequence containing a variety of control elements such as promoters, enhancers, silencers and the like (hereafter collectively called a promoter), an adipocyte-specific promoter, or an inducible promoter.

In certain embodiments, the composition comprises a plasmid, the plasmid comprising the nucleic acid encoding the FSP27 protein operably linked to a promoter.

In certain embodiments, the composition comprises a viral vector, the viral vector comprising the nucleic acid encoding the FSP27 protein operably linked to a promoter.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 1A shows the sigmoid inhibition curve for HepG2-24 hr–IC50=65 nM; and, FIG. 1B shows % inhibition for HepG2-24 hr.

FIG. 2A shows the sigmoid inhibition curve for PANC1-24 hr–IC50=132 nM; and, FIG. 2B shows % inhibition for PANC1-24 hr.

FIG. 3A shows the sigmoid inhibition curve for MCF7-24 hr–IC50=187 nM; and, FIG. 3B shows % inhibition for MCF7-24 hr.

FIG. 4A shows the sigmoid inhibition curve for 786-O-24 hr–IC50>400 nM; and, FIG. 4B shows % inhibition for 786-O-24 hr.

FIG. 5A shows the sigmoid inhibition curve for SK-MEL-28–24 hr–IC50>400 nM; and, FIG. 5B shows % inhibition for SK-MEL-28-24 hr.

FIG. 7A shows % inhibition for HepG2 following 24 hr exposure; and, FIG. 7B shows % inhibition for HepG2 after additional 24 hours following removal of CIDEC (post CIDEC).

FIG. 8A shows % inhibition for SK-MEL-28 following 24 hr exposure; and, FIG. 8B shows % inhibition for SK-MEL-28 after additional 24 hours following removal of CIDEC (post CIDEC).

FIG. 13 discloses SEQ ID NO: 4.

FIG. 15: Table 1, showing the amino acid sequence detail of the relevant peptides.

DETAILED DESCRIPTION OF THE PREFERRED EMBODIMENT(S)

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Definitions

In order to facilitate review of the various embodiments of the disclosure, the following explanations of specific terms are provided:

FSP27: Refers to Fat Specific Protein 27, as well as any other accepted nomenclature for the gene in human or other non-human species, including but not limited to CIDEC, Cidec, Cide-C, and Cide-3.

FSP27 Compositions/Medicaments: Refers to the FSP27 as shown in the schematic representation of FSP27 fragments in FIG. 12A, the amino acids listed in FIG. 14, and the amino acid sequences listed in FIG. 15, including any substitutions, deletions, modifications, or mutations thereof.

Figure 14:
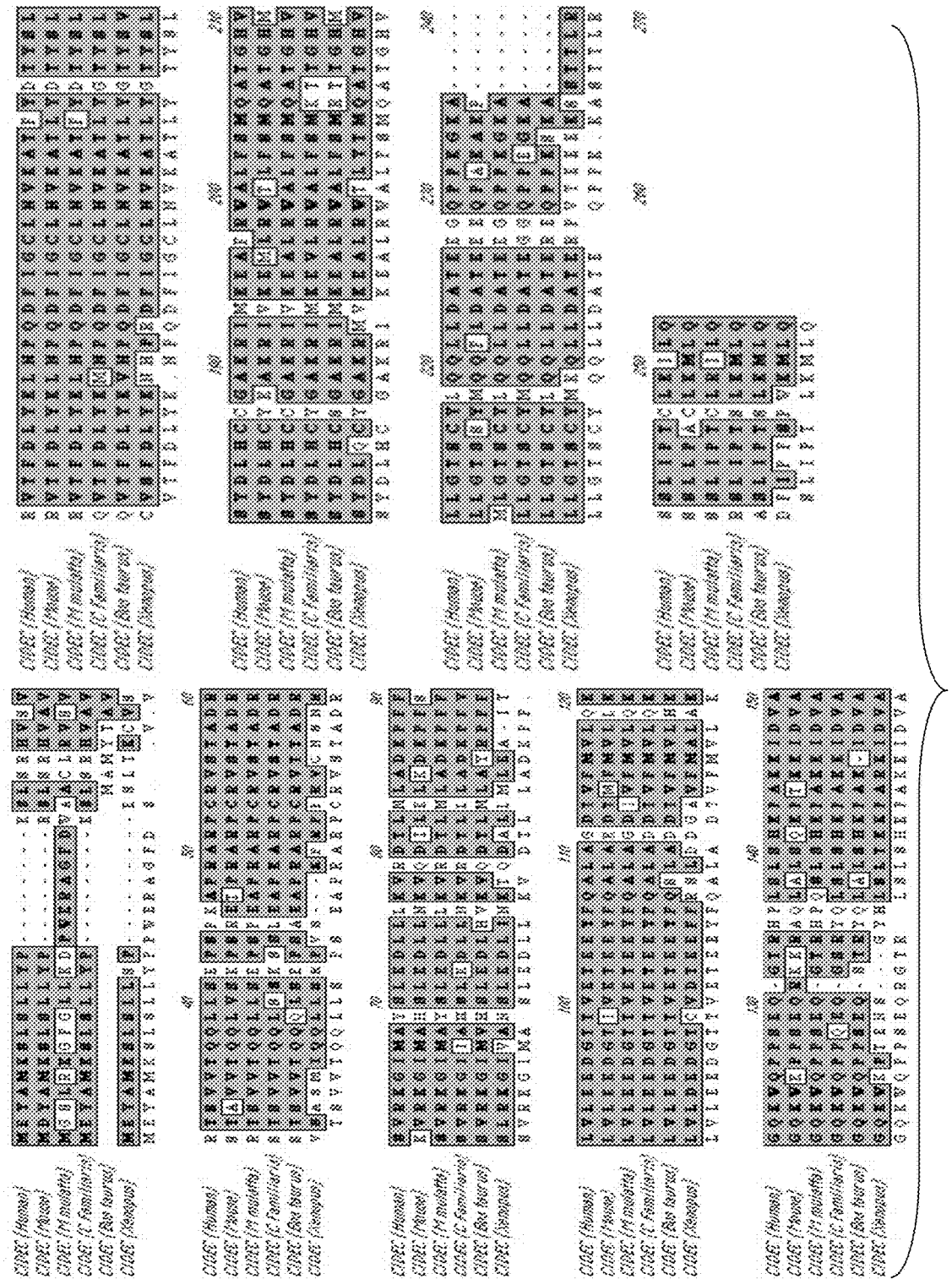
FIG. 14: FSP27 sequence is conserved in vertebrates; for example, >90% conserved sequence in FSP27 in humans (SEQ ID NO: 12), mouse (SEQ ID NO: 13), monkey (SEQ ID NO: 14), dog (SEQ ID NO: 15), cow (SEQ ID NO: 16) and frog (SEQ ID NO: 17).

FSP27 Compositions/Medicaments as contemplated herein may also be prepared as recombinant proteins, including the FSP27 sequences shown in FIG. 14, and in the Table in FIG. 15.

The FSP27 protein is encoded by a nucleic acid sequence or gene. As used herein, a "nucleic acid" or "polynucleotide" includes a nucleic acid, an oligonucleotide, a nucleotide, a polynucleotide, and any fragment or variant thereof. The nucleic acid or polynucleotide may be double-stranded, single-stranded, or triple-stranded DNA or RNA (including cDNA), or a DNA-RNA hybrid of genetic or synthetic origin, wherein the nucleic acid contains any combination of deoxyribonucleotides and ribonucleotides and any combination of bases, including, but not limited to, adenine, thymine, cytosine, guanine, uracil, inosine, and xanthine hypoxanthine. The nucleic acid or polynucleotide may be combined with a carbohydrate, lipid, protein, or other materials. Preferably, the nucleic acid encodes FSP27 protein.

The "complement" of a nucleic acid refers, herein, to a nucleic acid molecule with sufficient homology to recognize, or which will hybridize to another nucleic acid under conditions of high stringency. High-stringency conditions are known in the art (see e.g., Maniatis et al., Molecular Cloning: A Laboratory Manual, 2nd ed. (Cold Spring Harbor: Cold Spring Harbor Laboratory, 1989) and Ausubel et al., eds., Current Protocols in Molecular Biology (New York, N.Y.: John Wiley & Sons, Inc., 2001)). Stringent conditions are sequence-dependent, and may vary depending upon the circumstances. As used herein, the term "cDNA" refers to an isolated DNA polynucleotide or nucleic acid molecule, or any fragment, derivative, or complement thereof. It may be double-stranded, single-stranded, or triple-stranded, it may have originated recombinantly or synthetically, and it may represent coding and/or noncoding 5' and/or 3' sequences.

In addition, "complementary" means not only those that are completely complementary to a region of at least 15 continuous nucleotides, but also those that have a nucleotide sequence homology of at least 40% in certain instances, 50% in certain instances, 60% in certain instances, 70% in certain instances, at least 80%, 90%, and 95% or higher. The degree of homology between nucleotide sequences can be determined by various methods, including an algorithm, BLAST, etc.

As used herein, nucleic acids and/or nucleic acid sequences are "homologous" when they are derived, naturally or artificially, from a common ancestral nucleic acid or nucleic acid sequence. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95%, 96%, 97%, 98%, or 99% or more can also be used to establish homology. Methods for determining sequence similarity percentages (e.g., BLASTN using default parameters) are generally available. Software for performing BLAST analyses is publicly available through the National Center for Biotechnology Information.

The nucleic acid agent, for example, may be a plasmid. Such a plasmid may comprise a nucleic acid sequence encoding FSP27, variants or isoforms thereof, although it is to be understood that other types of nucleic acid agents, such as recombinant viral vectors, may also be used for the purposes of the present invention. In one embodiment of the present invention, the nucleic acid (e.g., plasmid) encodes at least one FSP27 variant or isoform.

The term "plasmid", as used herein, refers generally to circular double-stranded DNA, which is not bound to a chromosome. The DNA, for example, may be a chromosomal or episomal-derived plasmid. The plasmid of the present invention may optionally contain an initiator or promoter of transcription, terminator of transcription, translational control sequences, and/or a discrete series of restriction-endonuclease recognition sites, located between the promoter and the terminator. In the plasmid, a polynucleotide insert of interest (e.g., one encoding a FSP27-associated protein) should be operatively linked to an appropriate promoter. The promoter may be its native promoter or a host-derived promoter. The promoter may also be a tissue-specific promoter, such as an adipocyte-specific promoter or other tissue-specific promoter. The promoter may further be a regulatable promoter, which may be turned off when the expression of the gene is no longer desired. Non-limiting examples of promoters for use in the present invention include the actin promoter and viral promoters. Other suitable promoters will be known to the skilled artisan.

Therapeutic: A generic term that includes both diagnosis and treatment. It will be appreciated that in these methods the "therapy" may be any therapy for treating a disease including, but not limited to, pharmaceutical compositions, gene therapy and biologic therapy such as the administering of antibodies and chemokines. Thus, the methods described herein may be used to evaluate a patient or subject before, during and after therapy, for example, to evaluate the reduction in disease state.

Adjunctive therapy: A treatment used in combination with a primary treatment to improve the effects of the primary treatment.

Clinical outcome: Refers to the health status of a patient following treatment for a disease or disorder or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Decrease in survival: As used herein, "decrease in survival" refers to a decrease in the length of time before death of a patient, or an increase in the risk of death for the patient.

Patient: As used herein, the term "patient" includes human and non-human animals. The preferred patient for treatment is a human. "Patient," "individual" and "subject" are used interchangeably herein.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Poor prognosis: Generally refers to a decrease in survival, or in other words, an increase in risk of death or a decrease in the time until death. Poor prognosis can also refer to an increase in severity of the disease, such as an increase in spread (metastasis) of the cancer to other tissues and/or organs.

Screening: As used herein, "screening" refers to the process used to evaluate and identify candidate agents that affect such disease.

Comprising, comprises and comprised of: As used herein are synonymous with "including", "includes" or "containing", "contains", and are inclusive or open-ended and do not exclude additional, non-recited members, elements or method steps. The terms "comprising", "comprises" and "comprised of" also include the term "consisting of".

About: As used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

And/or: When used in a list of two or more items, means that any one of the listed items can be employed by itself or any combination of two or more of the listed items can be employed. For example, if a list is described as comprising group A, B, and/or C, the list can comprise A alone; B alone; C alone; A and B in combination; A and C in combination; B and C in combination; or A, B, and C in combination.

EXAMPLES

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Cell Culture and Treatments

Human cancer cell lines (part of NCI-60 panel of human cancer cells)—SK-MEL-5 (melanoma), SK-MEL-28 (melanoma), MCF-7 (breast cancer), 786-0 (renal cancer), A498 (renal cancer), Hep-G2 (liver cancer), SK-HEP-1 (liver cancer), PANC-1 (pancreatic cancer), and normal human skin fibroblast cells MALME-3 cells were obtained from American Type Culture Collection (ATCC; Manassas, Va.). The cells were grown and maintained in corresponding complete growth medium—PANC-1 in DMEM medium (ATCC), 786-0 in RPMI-1640 medium, remaining cell lines in EMEM media (ATCC), and MALME-3 in McCoy's medium (ATCC)—as indicated by ATCC protocols. Complete growth media was supplemented with 10% fetal bovine serum (FBS; ATCC) and 1× antibiotic-antimycotic (Thermo Fisher Scientific, Waltham, Mass.). MALME-3 cells were grown in McCoy's medium (ATCC) supplemented with 15% FBS and 1× antibiotic-antimycotic. Cells were grown at 37 C/5% $CO_2$ in a humidified incubator. Media was replaced every third day.

Recombinant hGH was purchased from Antibodies Online (Atlanta, Ga.), GH antagonist (GHA; Somavert) was obtained from Pfizer (New York City, N.Y.), full length CIDEC was purchased from Abcam (Cambridge, UK) and CIDEC fragment peptides were synthesized at Genscript (Piscataway, N.J.). No hGH or GHA was present in the media or added externally unless specifically mentioned. For hGH treatment, 16 hr. after cell seeding (or 24 hr. post-transfection), any GH or GHA or CIDEC or peptides were added at specific concentrations. Cells were subsequently incubated for 48 hr. before subsequent analyses.

Cell Viability Assay

A resazurin based absorption assay was performed measuring cell proliferation, as a measure of inhibition of cell growth/viability. There are several commonly practiced assays using tetrazolium (MTT, MTS, XTT), or resazurin which give a quantitative reflection of cell viability. Although ATP detection assay is the most sensitive of the available options, resazurin-based assay is considered adequate and is routinely used to measure compound EC50s or cell viability following cytotoxic treatments. A stock solution of 1% (w/v) resazurin (Sigma-Aldrich #R7017) in 1×PBS was made and filter-sterilized. The final concentration of resazurin in the assay was 0.004%. Proliferating cells can be quantified by spectrophotometric measurement of a bright pink fluorescent product called resorufin (stable for >4 hr) formed when mildly fluorescent blue resazurin enters a reducing intracellular environment characteristic of proliferating cells. Cells were seeded at 10,000 cells/$cm^2$ into 96-well plates and transfected as described above. The resazurin assay was performed following the respective treatment periods and resorufin absorbance was measured at 570 nm (reference wavelength=600 nm) using Spectramax250 (Molecular Devices, Sunnyvale, Calif.) and SoftmaxPro software. In all cases, cells were incubated at 37 C/5% $CO_2$ for 1 hr following resazurin addition. The resazurin assay for cell proliferation was used to measure EC-50 of relevant drugs and Graph Pad Prism was used to calculate EC-50 shifts (EC50 shift=EC50 of treated cell line/EC50 of parental cell line.

A 1% (w/v) resazurin (Sigma-Aldrich) solution in 1×PBS was made and filter-sterilized. The final concentration of resazurin in the assay was 0.004%. Inside the proliferating cells mildly fluorescent blue resazurin is reduced to a bright pink fluorescent product called resorufin (stable for 4 hr), which is a quantitative measure of the percentage of proliferating cells. In all cases, cells were incubated at 37 C/5% $CO_2$ for 45-60 minutes for adequate sensitivity of detection. Briefly, cells were seeded at 10,000 cells/$cm^2$ into 96-well plates and transfected as described above. The resazurin assay was performed 60 hr after transfection (unless specified otherwise) and resorufin absorbance was measured at 570 nm (reference wavelength=600 nm) using Spectramax250 (Molecular Devices) and SoftmaxPro v4.7.1 software.

Statistical Analyses

Parametric and non-parametric statistical analyses were done using R software (ver3.0.2). For resazurin based assays a paired students T-test and ANOVA was performed (using GraphPad Prism software) to compare for significance ($p<0.05$ is considered significant).

Example 1—Anti-Cancer Effect of Exogenously Added CIDEC

To confirm if human full-length CIDEC protein had a dose dependent effect in cell viability inhibition of different classes of cancer cells, a 10-dose treatment was used for 24 hr (or 48 hr) with a maximum concentration of 400 nM CIDEC. Dose response analysis of cancers of breast, liver, pancreas, renal and melanoma, and normal human cells against 0-400 nM of CIDEC indicate a variable effect of CIDEC in different cancer types.

Figure 1A:
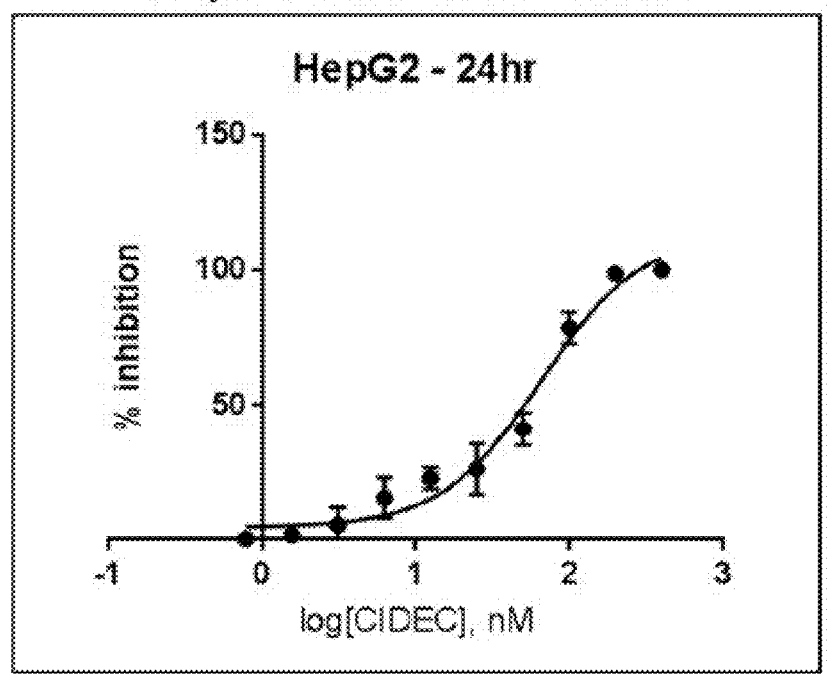
FIGS. 1A-1B: Effect of CIDEC on human liver cancer cell viability; Type: human hepatocellular carcinoma (HCC); Cell: HepG2; Assay: Cell viability assay (Presto-Blue, Invitrogen); Doses (nM): 0-400; Treatment period (hr): 24.
Figure 1B:
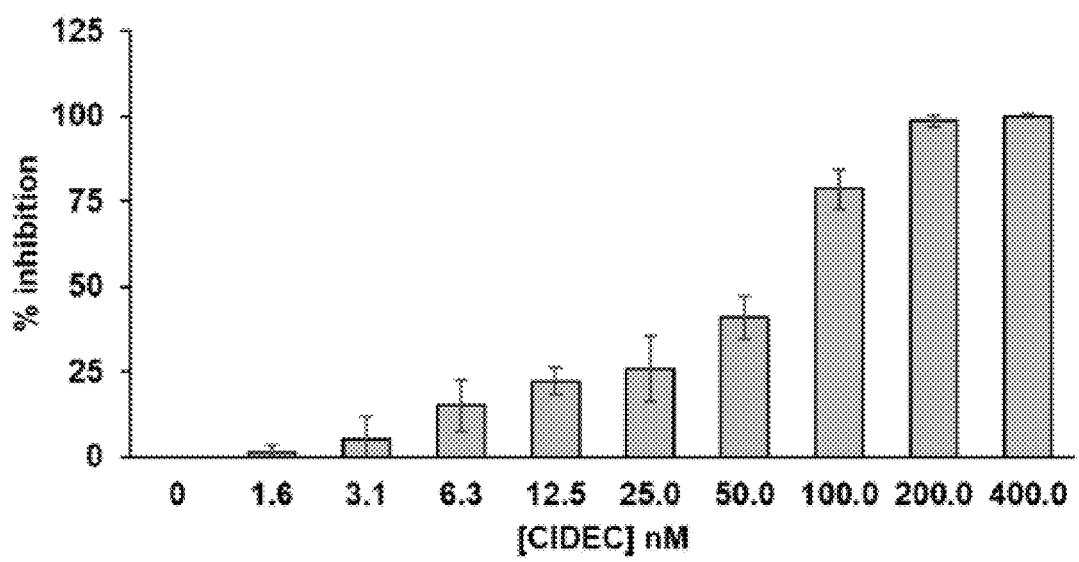

FIGS. 1A-1B show that human liver cancer (HepG2—hepatocellular carcinoma or HCC) cells were found to be significantly responsive to the effects of CIDEC. HepG2 cells had an EC50 (dose that causes 50% decrease of cell viability)=65 nM.

Figure 2A:
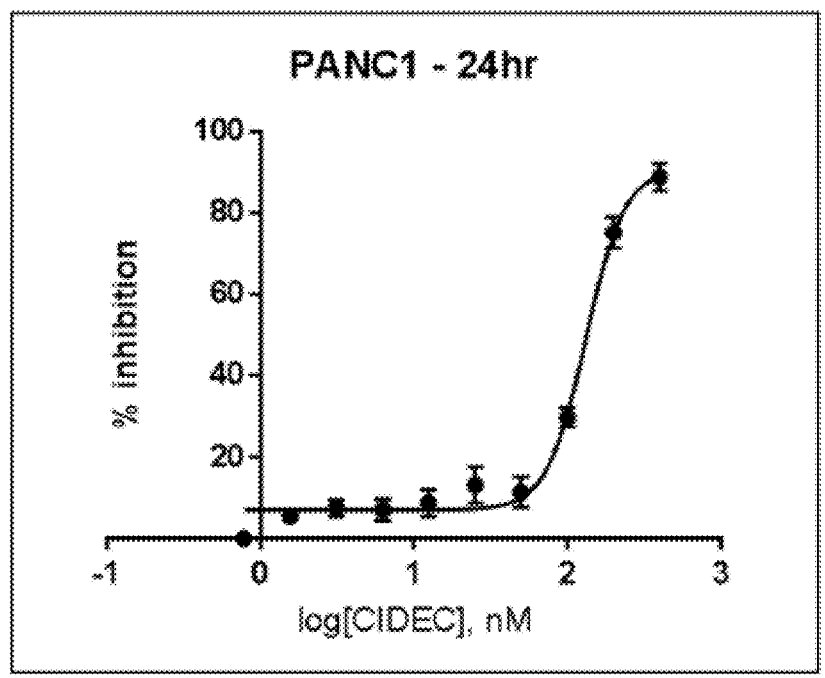
FIGS. 2A-2B: Effect of CIDEC on human pancreatic cancer cell viability; Type: human pancreatic ductal adenocarcinoma (PDAC); Cell: PANC-1; Assay: Cell viability assay (Presto-Blue, Invitrogen); Doses (nM): 0-400; Treatment period (hr): 24.
Figure 2B:
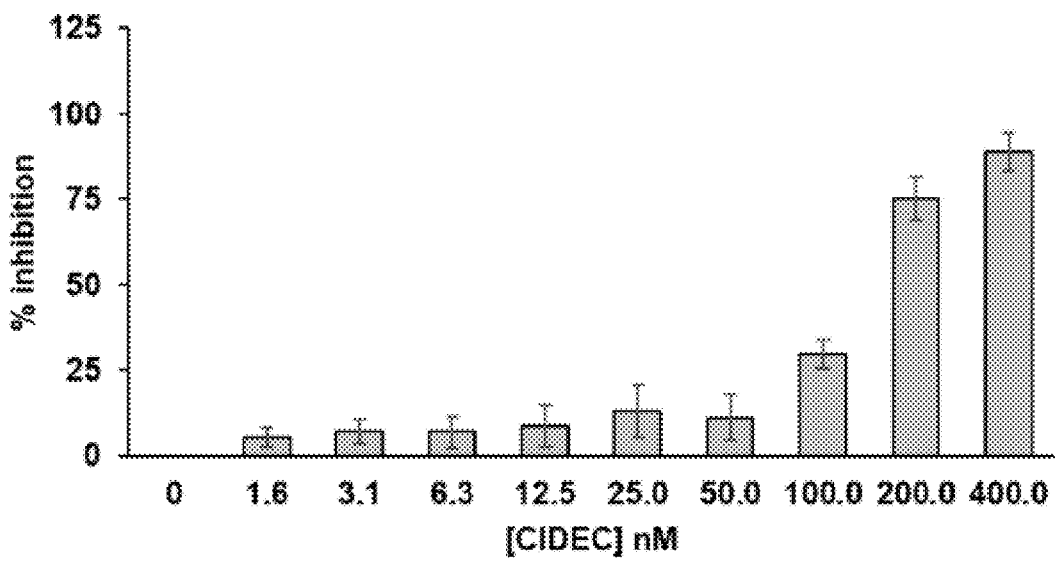

FIGS. 2A-2B show that human pancreatic cancer (PANC-1—pancreatic ductal adenocarcinoma or PDAC) cells were found to be sensitive to the effects of CIDEC. PANC1 cells had an EC50=132 nM.

Figure 3A:
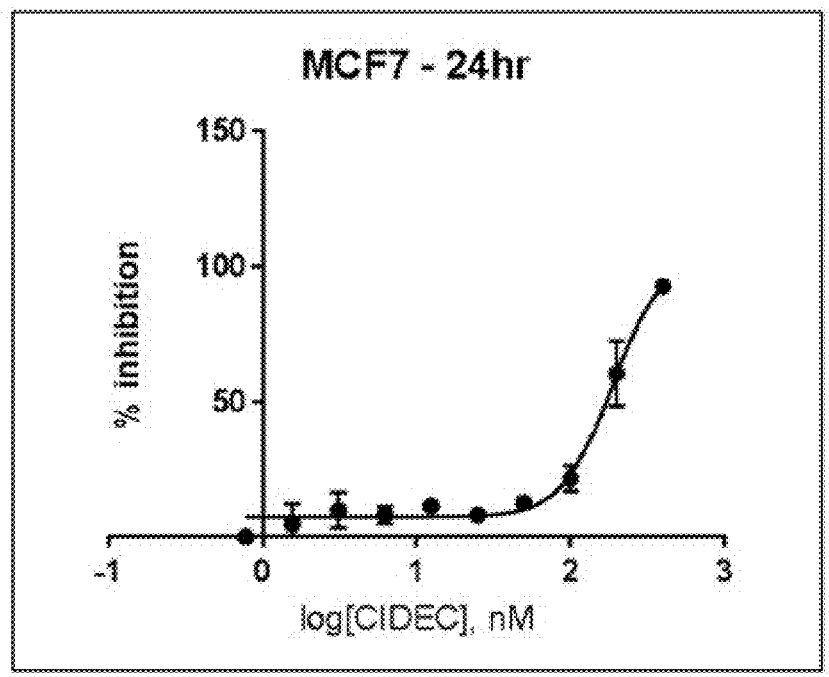
FIGS. 3A-3B: Effect of CIDEC on human breast cancer cell viability; Type: human breast cancer; Cell: MCF7; Assay: Cell viability assay (Presto-Blue, Invitrogen); Doses (nM): 0-400; Treatment period (hr): 24.
Figure 3B:
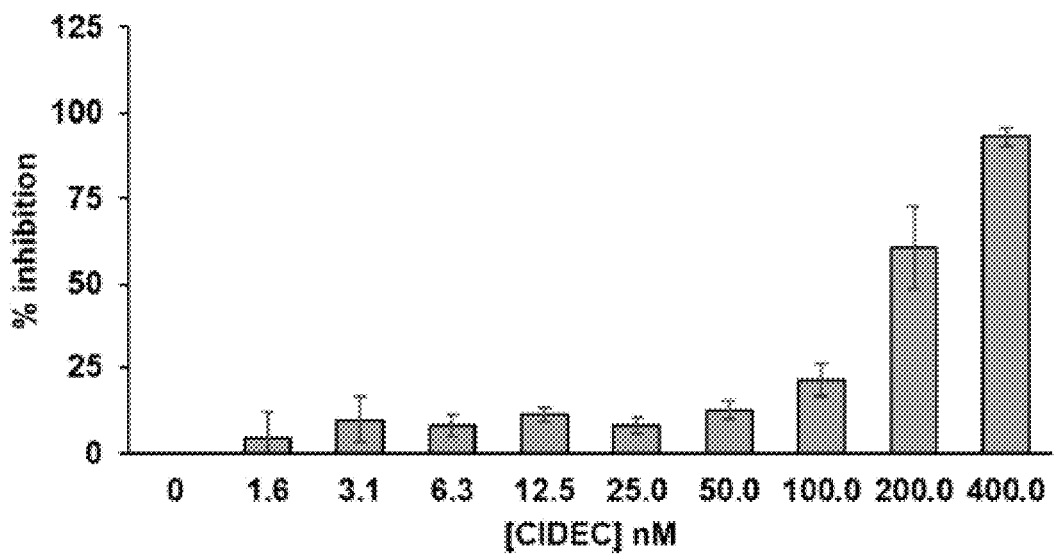

FIGS. 3A-3B show that human breast cancer (BC) cells were also found to be responsive to the effects of CIDEC. MCF7 cells had an EC50=187 nM.

Figure 4A:
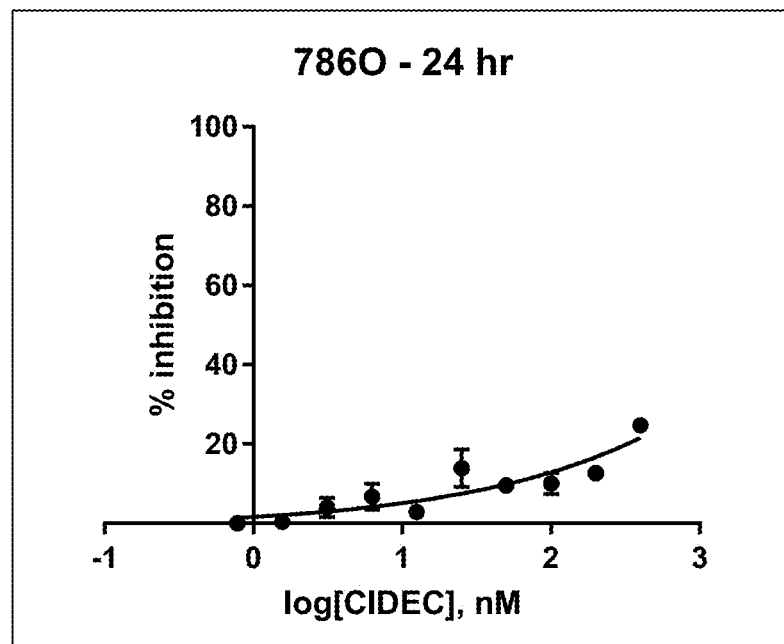
FIGS. 4A-4B: Effect of CIDEC on human renal cancer cell viability; Type: human clear cell renal cell carcinoma (ccRCC); Cell: 786-O; Assay: Cell viability assay (Presto-Blue, Invitrogen); Doses (nM): 0-400; Treatment period (hr): 24.
Figure 4B:
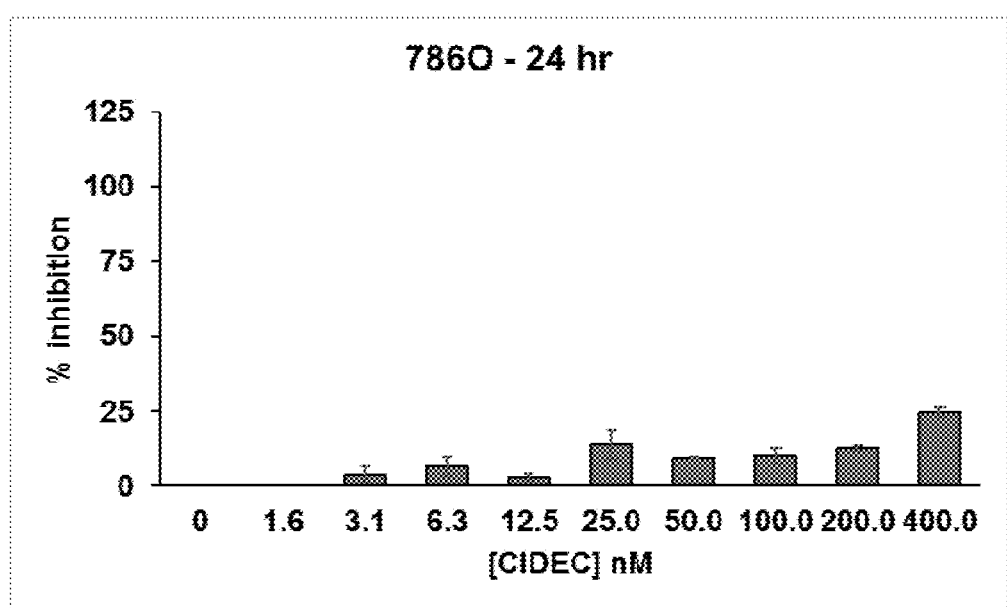

FIGS. 4A-4B show that human renal cancer cells (786-0) were found to be not responsive to the effects of CIDEC up to a dose of 400 nM. 786-0 cells had an EC50>400 nM.

Figure 5A:
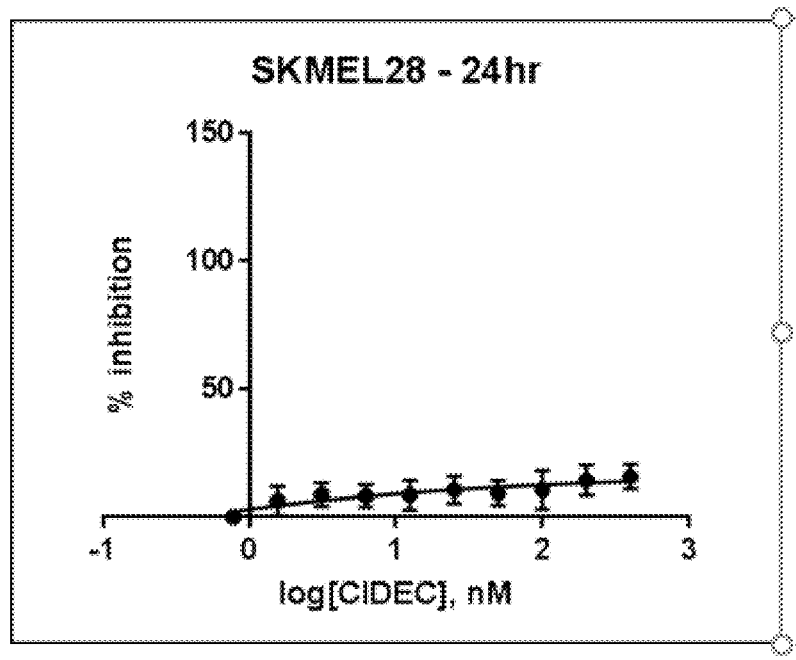
FIGS. 5A-5B: Effect of CIDEC on human melanoma cancer cell viability; Cell: human melanoma cancer (SK-MEL-28) cells; Assay: Cell viability assay (Presto-Blue, Invitrogen); Doses (nM): 0-400 nM; Treatment period (hr): 24.
Figure 5B:
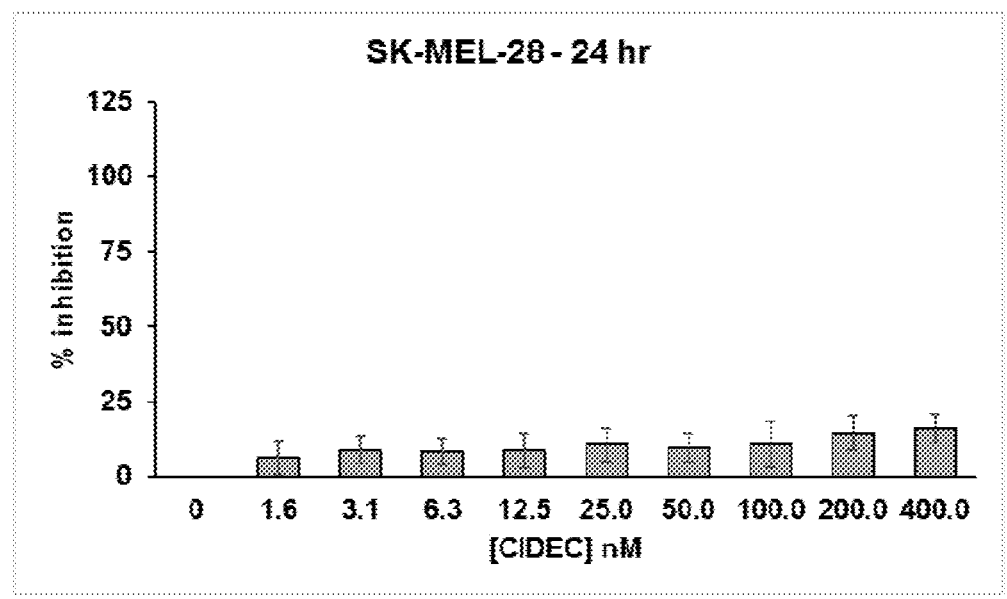

FIGS. 5A-5B shows that human melanoma cells (SK-MEL-28) were found to be not responsive to the effects of CIDEC up to a dose of 400 nM. SK-MEL-28 cells had an EC50>400 nM (FIG. 5).

Figure 6:
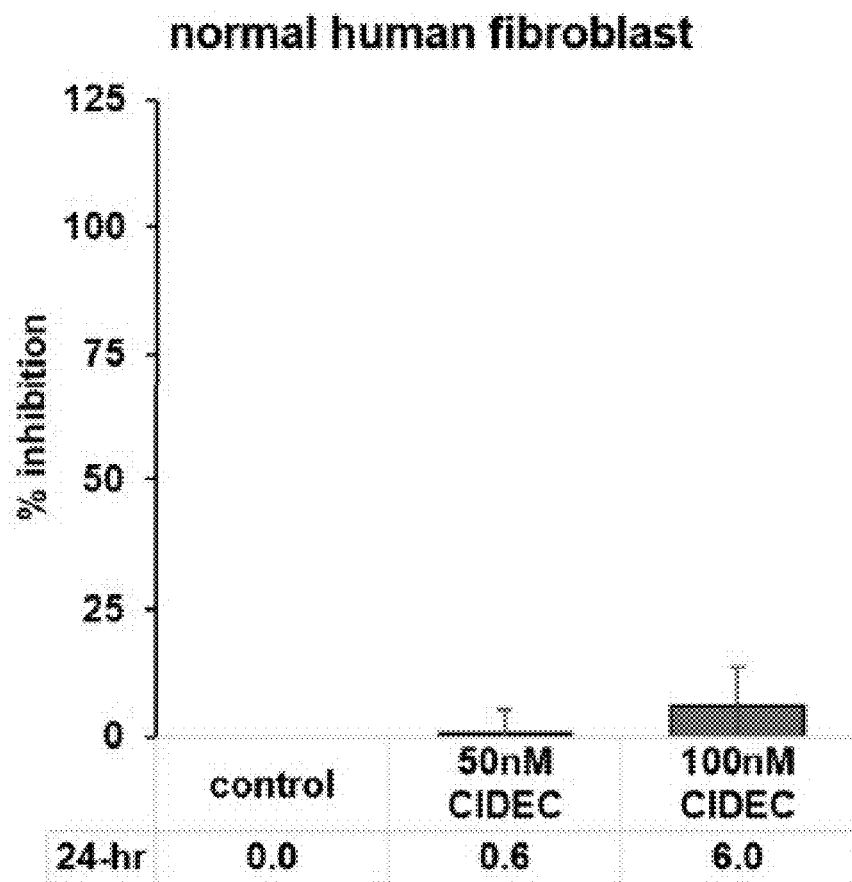
FIG. 6: Effect of CIDEC on human normal fibroblast cells; Cell: human normal fibroblast cells; Assay: Cell viability assay (Presto-Blue, Invitrogen); Doses (nM): 0, 50, 100 nM; Treatment period (hr): 24.

FIG. 6 shows that human normal fibroblast cells showed no significant decrease in cell viability on exposure to up to 100 nM CIDEC.

Example 2—Synthetic Lethality

To confirm if human full-length CIDEC protein had synthetic lethality or a syngenic effect in inhibiting cancer cell viability, when administered with established or prescribed anti-cancer drugs, we treated human melanoma, liver or renal cancer cells with 50 nM CIDEC and different types of anti-cancer drugs for 48 hr. CIDEC did not improve drug effects in case of human melanoma, but showed significant increase in efficacy of sorafenib-tosylate against liver cancer.

Figure 7A:
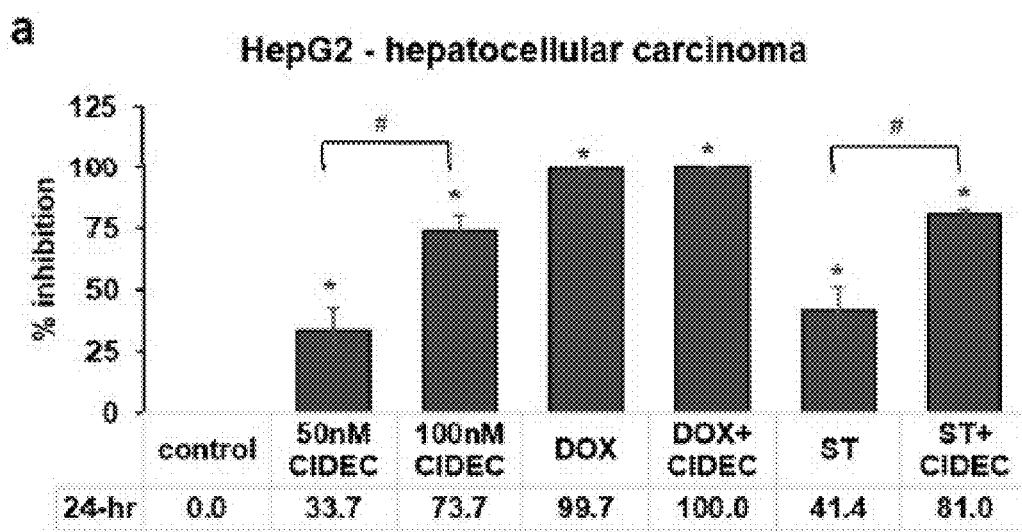
FIGS. 7A-7B: Effect of CIDEC and anti-cancer drugs on human liver cancer cell viability; Type: human hepatocellular carcinoma (HCC); Cell: HepG2; Assay: Cell viability assay (Presto-Blue, Invitrogen); Doses (nM): 0, 50, 100 nM; Treatment period (hr): 24, and +24 after removing CIDEC (post CIDEC); Drugs: Doxorubicin (DOX) @ 300 nm; Sorafenib tosylate (ST) @ 1000 nm.
Figure 7B:
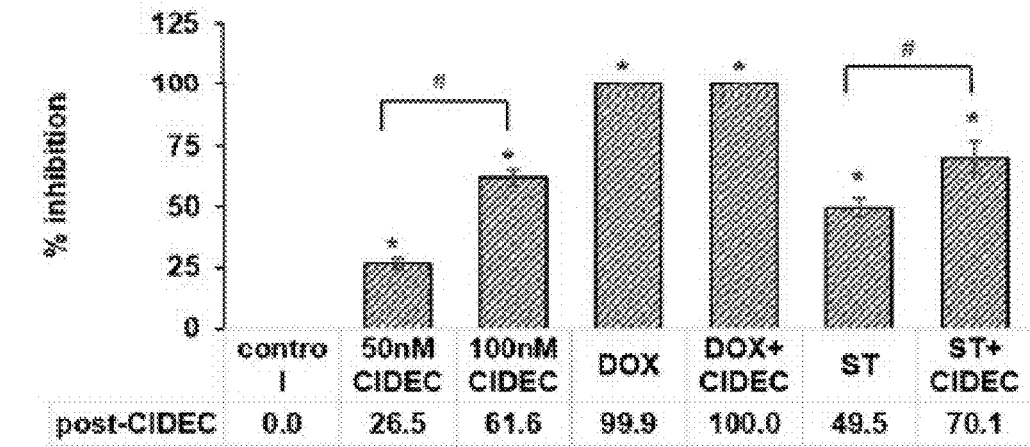

FIGS. 7A-7B show co-administration and 24 hr treatment with full-length CIDEC (fl-CIDEC) caused a significant (2-fold) decrease in cell viability of liver cancer cells treated with sorafenib-tosylate. A similar effect was not seen for doxorubicin, because of supra-EC50 level of doxorubicin (300 nM) used for HepG2 cells (doxorubicin EC50 for HepG2=190 nM), which killed>90% cells even in absence of CIDEC.

Figure 8A:
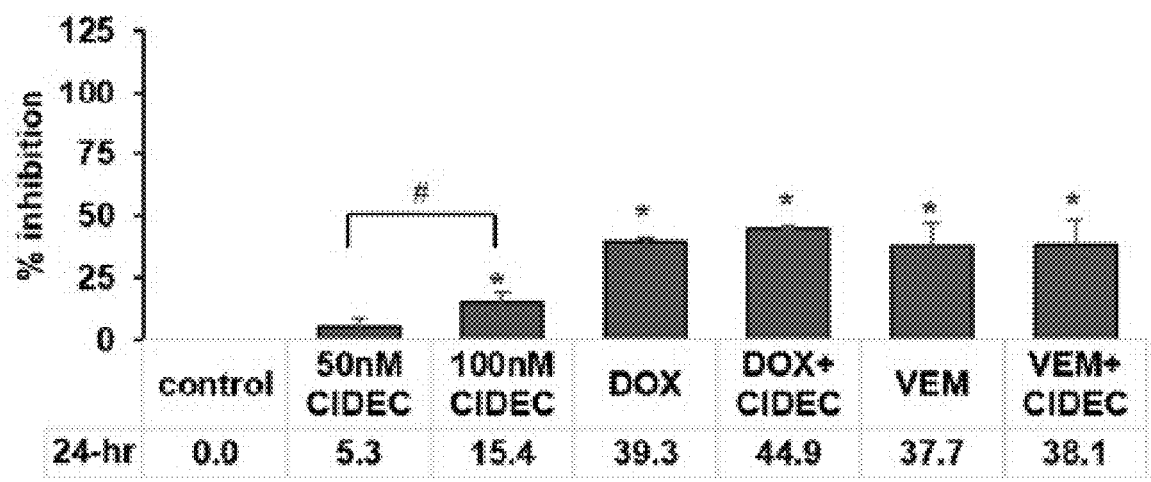
FIGS. 8A-8B: Effect of CIDEC and anti-cancer drugs on human melanoma cell viability; Type: human melanoma; Cell: SK-MEL-28; Assay: Cell viability assay (Presto-Blue, Invitrogen); Doses (nM): 0, 50, 100; Treatment period (hr): 24, +24 after removing CIDEC (post CIDEC); Drugs: Doxorubicin (DOX) @ 300 nm; Vemurafenib (VEM) @ 50 nm.
Figure 8B:
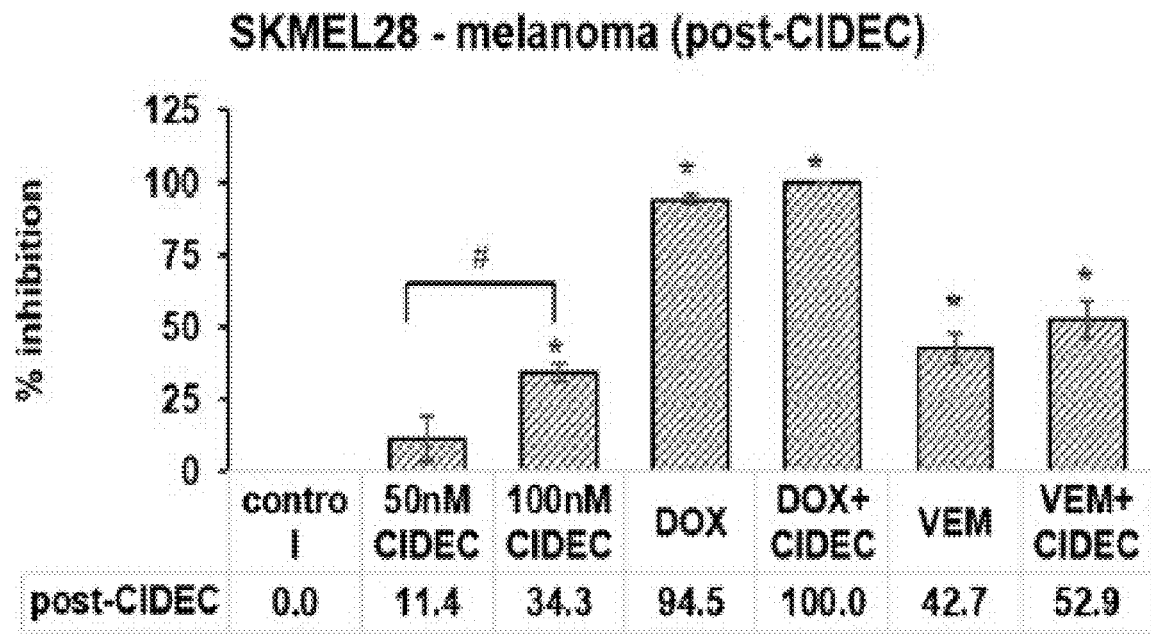

FIGS. 8A-8B show co-administration and 24 hr treatment with full-length CIDEC (fl-CIDEC) did not improve the cell inhibition rate of human melanoma cells above that of doxorubicin or vemurafenib.

Example 3—Anti-Cancer Effect of Exogenously Added CIDEC Fragment Peptides

To confirm the residues in human full-length CIDEC protein critical for the anti-cancer effects, we designed six peptides of varying length (See FIG. 15—Table 1 for details). Human melanoma (SK-MEL-28) or liver cancer (HepG2) cells were treated with 50 or 100 nM fl-CIDEC or the fragment peptides for 48 hr. The fragments had variable effects on cancer cell viability, with fragment #3 showing maximum inhibition, followed by fragments #2 and #4.

Figure 9:
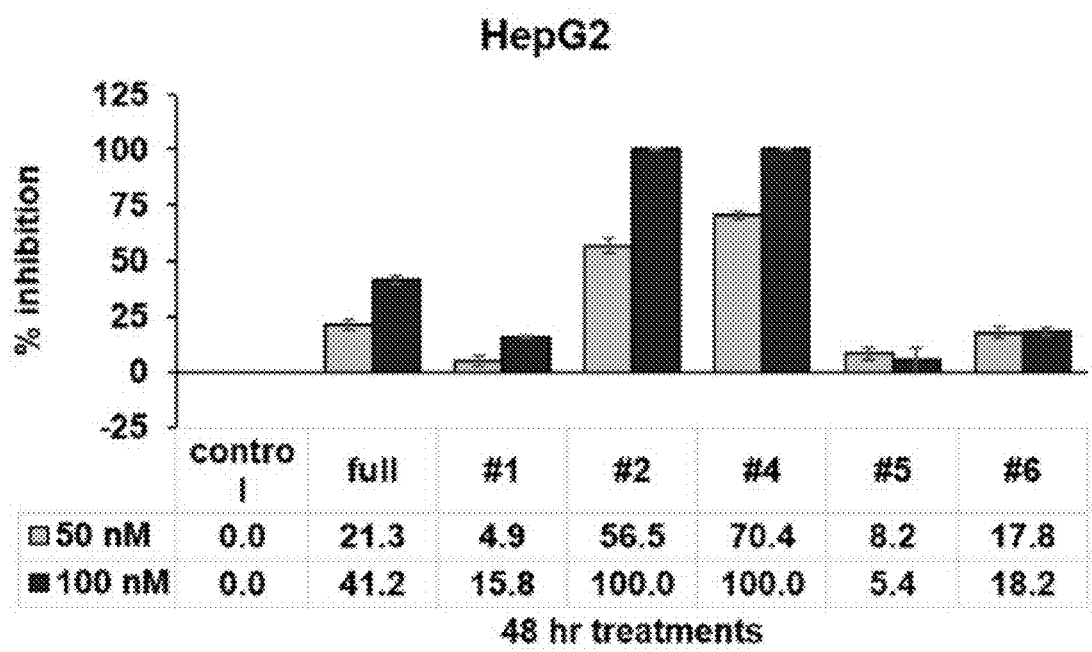
FIG. 9: Effect of CIDEC and fragment peptides on human liver cancer cell (HepG2) viability. [full-length CIDEC, #1, #2, #4, #5, #6=shorter fragment peptides of full-length CIDEC]; Cell: human liver cancer cells HepG2; Assay: Cell viability assay (Presto-Blue, Invitrogen); Doses (nM): 0, 50, 100; Treatment period (hr): 48.
Figure 10:
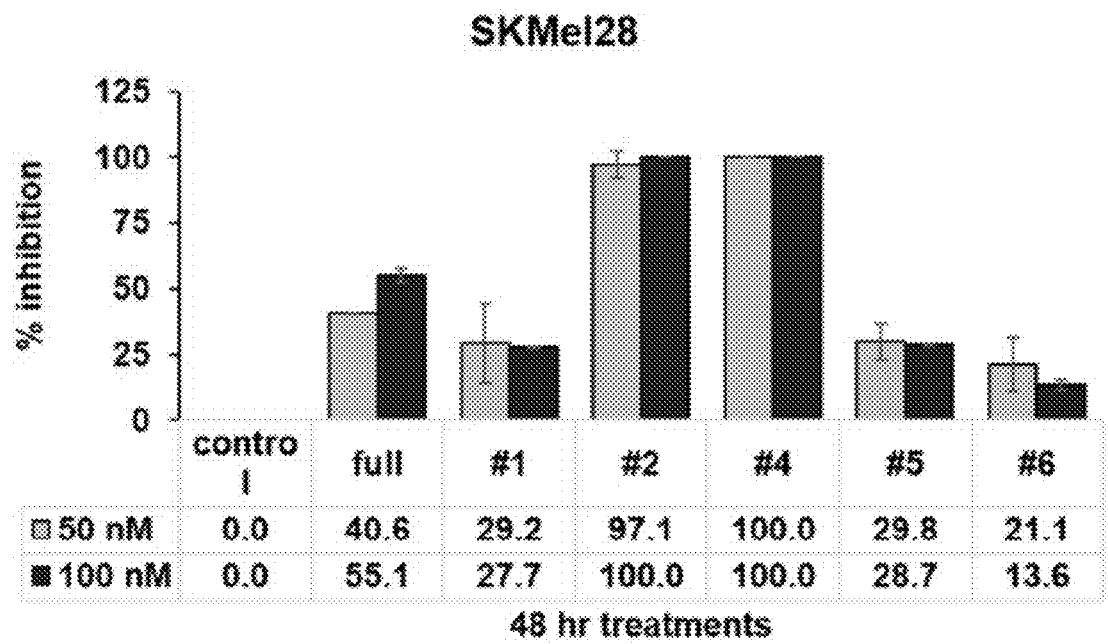
FIG. 10: Effect of CIDEC and fragment peptides on human melanoma cell (SK-MEL-28) viability. [full-length CIDEC, #1, #2, #4, #5, #6=shorter fragment peptides of full-length CIDEC]; Cell: human melanoma cells SK-MEL-28; Assay: Cell viability assay (Presto-Blue, Invitrogen); Doses (nM): 0, 50, 100; Treatment period (hr): 48.
Figure 11:
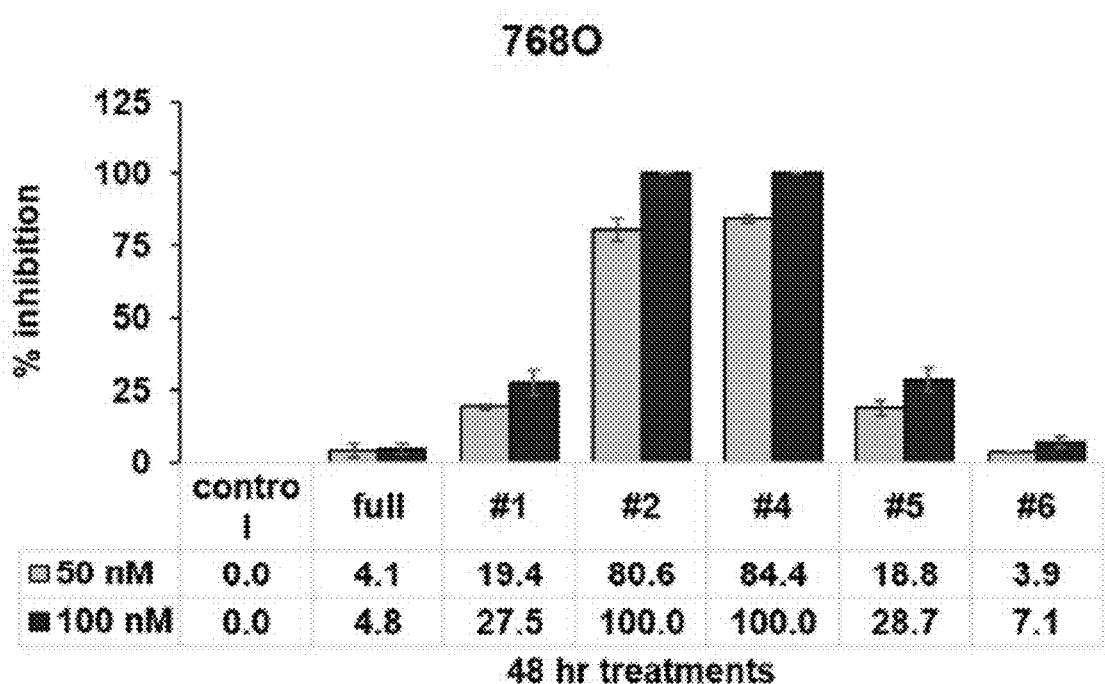
FIG. 11: Effect of CIDEC and fragment peptides on human renal cancer cell (786-O) viability. full-length CIDEC, #1, #2, #4, #5, #6=shorter fragment peptides of full-length CIDEC]; Cell: human renal cancer cells; Assay: Cell viability assay (Presto-Blue, Invitrogen); Doses (nM): 0, 50, 100; Treatment period (hr): 48.

FIGS. 9, 10 and 11 show CIDEC fragment number 2 and 4 (SEQ ID NOs: 2 and 4, respectively) was found to be highly efficacious in inhibiting cell viability of human cancers of liver, kidney and melanoma at 50 nM concentrations. Cf1, Cf5 and Cf6 showed lower activity than the fl-CIDEC.

FIG. 9 shows Cf4 and Cf2 were found to completely (100%) inhibit cell viability of cancers of human liver (HepG2) at 100 nM in 48 hr.

FIG. 10 shows Cf4 and Cf2 were found to completely (100%) inhibit cell viability of cancers of melanoma (SK-MEL-28) at 100 nM in 48 hr.

FIG. 11 shows Cf4 and Cf2 were found to completely (100%) inhibit cell viability of cancers of kidney (786-0) at 100 nM in 48 hr.

Figure 12A:
FIG. 12A: Schematic illustration of FSP27 fragments/mutants: FSP27 (120-239); FSP27 (120-220); FSP27 (120-210); and, FSP27 (140-210).
Figure 12A:
Figure 12A:
Figure 12A:

FIG. 12A: Schematic illustration of FSP27 fragments/mutants: FSP27 (120-239); FSP27 (120-220); FSP27 (120-210); and, FSP27 (140-210).

Figure 12B:
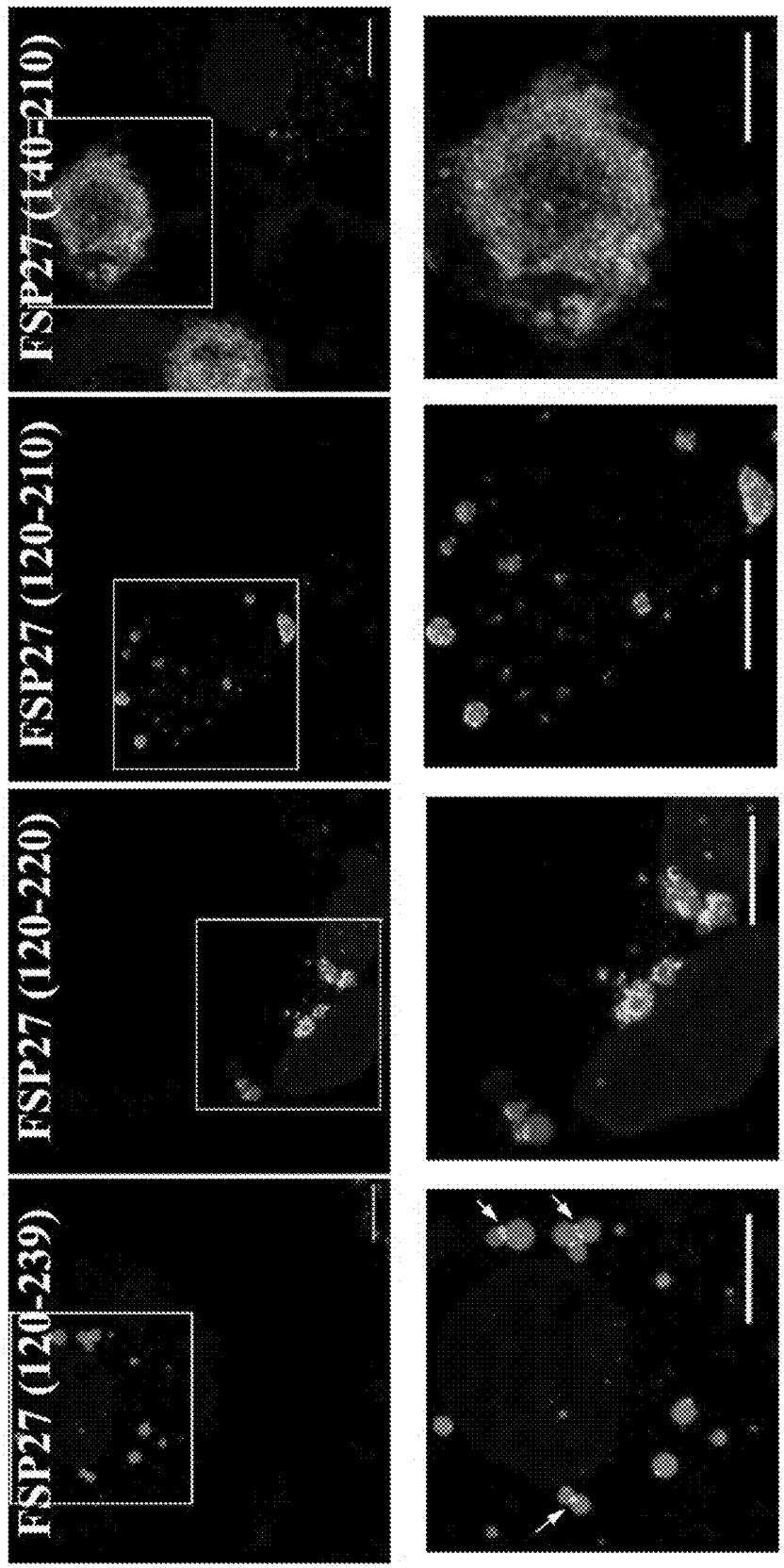
FIG. 12B: Expression of GFP fusion constructs of these deletions in COS7 cells; the images show the distribution of mutants (green) after 16 hr of transfection; Cells were labeled with Nile red (red), and nucleus was labeled with DAPI (blue).

FIG. 12B: Expression of GFP fusion constructs of these deletions in COS7 cells; the images show the distribution of mutants (green) after 16 hr of transfection; Cells were labeled with Nile red (red), and nucleus was labeled with DAPI (blue).

Figure 13:
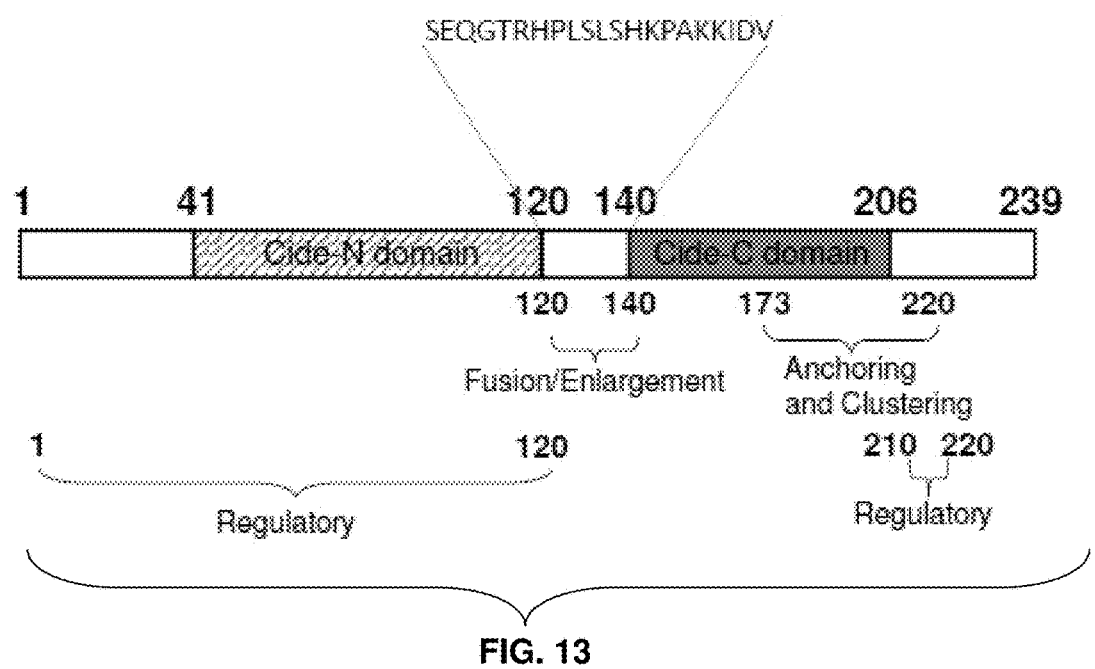
FIG. 13: Schematic illustration of full length FSP27 showing domains associated with lipid droplet dynamics.

FIG. 13: Schematic illustration of full length FSP27 showing domains associated with lipid droplet dynamics, and the segment 120-140 that has shown maximum efficacy towards anti-cancer effect in cells.

FIG. 14 shows that the FSP27 sequence is conserved in vertebrates; for example, >90% conserved sequence in FSP27 in humans, mouse, monkey, dog, cow and frog.

FIG. 15: Table 1, shows the amino acid sequence detail of the relevant peptides tested for anti-cancer activity in cells.

Other Examples

Pharmaceutical Compositions

A pharmaceutical composition as described herein may be formulated with any pharmaceutically acceptable excipients, diluents, or carriers. A composition disclosed herein may comprise different types of carriers depending on whether it is to be administered in solid, liquid, or aerosol form, and whether it needs to be sterile for such routes of administration as injection. Compositions disclosed herein can be administered in a suitable manner, including, but not limited to topically (i.e., transdermal), subcutaneously, by localized perfusion bathing target cells directly, via a lavage, in creams, in lipid compositions (e.g., liposomes), formulated as elixirs or solutions for convenient topical administration, formulated as sustained release dosage forms, or by other method or any combination of the forgoing as would be known to one of ordinary skill in the art (see, for example, Remington's Pharmaceutical Sciences, 2003, incorporated herein by reference).

The compositions provided herein are useful for treating animals, such as humans. A method of treating a human patient according to the present disclosure includes the administration of a composition, as described herein.

The phrases "pharmaceutical" or "pharmacologically acceptable" refer to molecular entities and compositions that produce no adverse, allergic, or other untoward reaction when administered to an animal, such as, for example, a human. A carrier or diluent may be a solid, semi-solid, or liquid material which serves as a vehicle, excipient, or medium for the active therapeutic substance. Some examples of the diluents or carriers which may be employed in the pharmaceutical compositions of the present disclosure are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol, and propellants such as trichloromonofluoromethane, dichlorodifluoromethane, and dichlorotetrafluoroethane.

The phrase "chemotherapeutic agent" refers to a therapeutic agent known to be used in treating a subject that has been diagnosed with cancer. Some examples of general classes of chemotherapeutic agents of the present disclosure include alkylating agents, anthracyclines, cytoskeletal disruptors, epothilones, histone deacetylase inhibitors, inhibitors of topoisomerase I and II, kinase inhibitors, nucleotide analogs and precursor analogs, peptide antibiotics, platinum-based agents, retinoids, and vina alkaloids and derivatives. Of these general classes, specific examples include but are not limite to doxorubicin (Adriamycin), sorafenib tosylate, cisplatin, paclitaxel, gemcitabine, vemurafenib, dabrafenib, linsitinib, crizotinib, and cabozantinib.

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols, and mixtures thereof, and in oils. Under ordinary conditions of storage and use, these preparations contain a preservative to prevent the growth of microorganisms. The pharmaceutical forms suitable for use include sterile aqueous solutions or dispersions and sterile powders for the extemporaneous preparation of sterile solutions or dispersions. In certain cases, the form should be sterile and should be fluid to the extent that easy injectability exists. It should be stable under the conditions of manufacture and storage and may optionally be preserved against the contaminating action of microorganisms, such as bacteria and fungi. The carrier can be a solvent or dispersion medium containing, for example, water, ethanol, a polyol (i.e., glycerol, propylene glycol, and liquid polyethylene glycol, and the like), suitable mixtures thereof, and/or vegetable oils. The prevention of the action of microorganisms can be brought about by various antibacterial and antifungal agents, for example, parabens, chlorobutanol, phenol, sorbic acid, thimerosal, and the like. In many cases, it may be preferable to include isotonic agents, such as, but not limited to, sugars or sodium chloride.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream, and petrolatum as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed time-period.

It is further envisioned the compositions disclosed herein may be delivered via an aerosol. The term aerosol refers to a colloidal system of finely divided solid or liquid particles dispersed in a liquefied or pressurized gas propellant. The typical aerosol comprises a suspension of active ingredients in liquid propellant or a mixture of liquid propellant and a suitable solvent. Suitable propellants include hydrocarbons and hydrocarbon ethers. Suitable containers can vary according to the pressure requirements of the propellant. Administration of the aerosol can vary according to subject's age, weight, and the severity and response of the symptoms.

Dosage

The actual dosage amount of a composition disclosed herein administered to an animal or human patient can be determined by physical and physiological factors such as body weight, severity of condition, the type of disease being treated, previous or concurrent therapeutic interventions, idiopathy of the patient, and the route of administration. Depending upon the dosage and the route of administration, the number of administrations of a preferred dosage and/or an effective amount may vary according to the response of the subject. The compounds of the present disclosure are generally effective over a wide dosage range. The practitioner responsible for administration can, in any event, determine the concentration of active ingredient(s) in a composition and appropriate dose(s) for the individual subject.

Naturally, the amount of active compound(s) in each therapeutically useful composition may be prepared in such a way that a suitable dosage can be obtained in any given unit dose of the compound. Factors such as solubility, bioavailability, biological half-life, route of administration, product shelf life, as well as other pharmacological considerations can be contemplated by those preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. The dosages can depend on many factors, and can in any event be determined by a suitable practitioner. Therefore, the dosages described herein are not intended to be limiting.

In some embodiments, the compositions further include an additional active ingredient. The preparation of a pharmaceutical composition that contains at least one compound or additional active ingredient can be known to those of skill in the art in light of the present disclosure, as exemplified by Remington's Pharmaceutical Sciences, 2003, incorporated herein by reference. Moreover, for animal (e.g., human) administration, it can be understood that preparations should meet sterility, pyrogenicity, and general safety and purity standards as required by the FDA Office of Biological Standards.

Packaging of the Composition

After formulation, the composition is packaged in a manner suitable for delivery and use by an end user. In one embodiment, the composition is placed into an appropriate dispenser and shipped to the end user. Examples of final container may include a pump bottle, squeeze bottle, jar, tube, capsule or vial.

The compositions and methods described herein can be embodied as parts of a kit or kits. A non-limiting example of such a kit comprises the ingredients for preparing a composition, where the containers may or may not be present in a combined configuration. In certain embodiments, the kits further comprise a means for administering the composition, such as a topical applicator, or a syringe. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A method for inhibiting cancer cell viability in a subject, comprising,
   contacting the cancer cell with a fat specific protein (FSP27) medicament or a pharmaceutically acceptable composition thereof, in an amount to decrease the cancer cell's viability;
   wherein the FSP27 fragment is Cf4 (SEQ ID NO: 4); and,
   wherein the cancer is one or more of: liver cancer, renal cancer and melanoma.

2. A method for inhibiting cancer cell viability in a subject, comprising,
   contacting the cancer cell with a fat specific protein (FSP27) medicament or a pharmaceutically acceptable composition thereof, in an amount to decrease the cancer cell's viability;
   wherein the FSP27 fragment is Cf2 (SEQ ID NO: 2); and,
   wherein the cancer is one or more of: liver cancer, renal cancer and melanoma.

3. The method of claim 1, wherein the cancer cell is a human cell.

4. The method of claim 2, wherein the cancer cell is a human cell.

* * * * *

```
                         SEQUENCE LISTING

<160> NUMBER OF SEQ ID NOS: 17

<210> SEQ ID NO 1
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Glu Tyr Ala Met Lys Ser Leu Ser Leu Leu Tyr Pro Lys Ser Leu
1               5                   10                  15

Ser Arg His Val Ser Val Arg Thr Ser Val Val Thr Gln Gln Leu Leu
            20                  25                  30

Ser Glu Pro Ser Pro Lys Ala Pro Arg Ala Arg Pro Cys Arg Val Ser
        35                  40                  45

Thr Ala Asp Arg Ser Val Arg Lys Gly Ile Met Ala
    50                  55                  60

<210> SEQ ID NO 2
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Tyr Asp Leu His Cys Cys Gly Ala Lys Arg Ile Met Lys Glu Ala Phe
1               5                   10                  15

Arg Trp Ala Leu Phe Ser Met Gln Ala Thr Gly His Val Leu Leu Gly
            20                  25                  30

Thr Ser Cys Tyr Leu Gln Gln Leu Leu Asp Ala Thr Glu Glu Gly Gln
        35                  40                  45

<210> SEQ ID NO 3
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Pro Arg Ala Arg Pro Cys Arg Val Ser Thr Ala Asp Arg Ser Val Arg
1               5                   10                  15
```

```
Lys Gly Ile Met Ala Tyr Ser Leu Glu Asp Leu Leu Lys Val Arg
            20                  25                  30

Asp Thr Leu Met Leu Ala Asp Lys Pro Phe Phe Leu Val Leu Glu Glu
        35                  40                  45

Asp Gly Thr Thr Val Glu Thr Glu Glu Tyr Phe Gln Ala Leu Ala Gly
 50                  55                  60

Asp Thr Val Phe Met Val Leu Gln Lys Gly Gln Lys Trp Gln Pro Pro
 65                  70                  75                  80

Ser

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Glu Gln Gly Thr Arg His Pro Leu Ser Leu Ser His Lys Pro Ala
 1               5                  10                  15

Lys Lys Ile Asp Val
            20

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Gln Leu Leu Asp Ala Thr Glu Glu Gly Gln
 1               5                  10

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Leu Leu Asp Ala Thr Glu Glu Gly Pro Pro Lys Gly Lys
 1               5                  10                  15

Ala Ser Ser Leu Ile Pro Thr Cys Leu Lys Ile Leu Gln
            20                  25

<210> SEQ ID NO 7
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ser Glu Gln Gly Thr Arg His Pro Leu Ser Leu Ser His Lys Pro Ala
 1               5                  10                  15

Lys Lys Ile Asp Val Ala Arg Val Thr Phe Asp Leu Tyr Lys Leu Asn
            20                  25                  30
```

```
Pro Gln Asp Phe Ile Gly Cys Leu Asn Val Lys Ala Thr Phe Tyr Asp
        35                  40                  45

Thr Tyr Ser Leu Ser Tyr Asp Leu His Cys Cys Gly Ala Lys Arg Ile
    50                  55                  60

Met Lys Glu Ala Phe Arg Trp Ala Leu Phe Ser Met Gln Ala Thr Gly
65                  70                  75                  80

His Val Leu Leu Gly Thr Ser Cys Tyr Leu Gln Gln Leu Leu Asp Ala
                85                  90                  95

Thr Glu Glu Gly Gln Pro Pro Lys Gly Lys Ala Ser Ser Leu Ile Pro
                100                 105                 110

Thr Cys Leu Lys Ile Leu Gln
            115

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Glu Gln Gly Thr Arg His Pro Leu Ser Leu
1               5                   10

<210> SEQ ID NO 9
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ser Glu Gln Gly Thr Arg His Pro Leu Ser Leu Ser His Lys Pro Ala
1               5                   10                  15

Lys Lys Ile Asp Val Ala Arg Val Thr Phe Asp Leu Tyr Lys Leu Asn
                20                  25                  30

Pro Gln Asp Phe Ile Gly Cys Leu Asn Val Lys Ala Thr Phe Tyr Asp
        35                  40                  45

Thr Tyr Ser Leu Ser Tyr Asp Leu His Cys Cys Gly Ala Lys Arg Ile
    50                  55                  60

Met Lys Glu Ala Phe Arg Trp Ala Leu Phe Ser Met Gln Ala Thr Gly
65                  70                  75                  80

His Val Leu Leu Gly Thr Ser Cys Tyr Leu Gln
                85                  90

<210> SEQ ID NO 10
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ser Glu Gln Gly Thr Arg His Pro Leu Ser Leu Ser His Lys Pro Ala
1               5                   10                  15

Lys Lys Ile Asp Val Ala Arg Val Thr Phe Asp Leu Tyr Lys Leu Asn
                20                  25                  30
```

```
Pro Gln Asp Phe Ile Gly Cys Leu Asn Val Lys Ala Thr Phe Tyr Asp
            35                  40                  45

Thr Tyr Ser Leu Ser Tyr Asp Leu His Cys Cys Gly Ala Lys Arg Ile
 50                  55                  60

Met Lys Glu Ala Phe Arg Trp Ala Leu Phe Ser Met Gln Ala Thr Gly
 65                  70                  75                  80

His Val Leu Leu Gly Thr Ser Cys Tyr Leu Gln Gln Leu Leu Asp Ala
                 85                  90                  95

Thr Glu Glu Gly Gln
            100
```

<210> SEQ ID NO 11
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Val Ala Arg Val Thr Phe Asp Leu Tyr Lys Leu Asn Pro Gln Asp Phe
 1               5                  10                  15

Ile Gly Cys Leu Asn Val Lys Ala Thr Phe Tyr Asp Thr Tyr Ser Leu
                 20                  25                  30

Ser Tyr Asp Leu His Cys Cys Gly Ala Lys Arg Ile Met Lys Glu Ala
             35                  40                  45

Phe Arg Trp Ala Leu Phe Ser Met Gln Ala Thr Gly His Val Leu Leu
 50                  55                  60

Gly Thr Ser Cys Tyr Leu Gln
 65                  70
```

<210> SEQ ID NO 12
<211> LENGTH: 238
<212> TYPE: PRT
<213> ORGANISM: Homo sapiens

<400> SEQUENCE: 12

```
Met Glu Tyr Ala Met Lys Ser Leu Ser Leu Leu Tyr Pro Lys Ser Leu
 1               5                  10                  15

Ser Arg His Val Ser Val Arg Thr Ser Val Val Thr Gln Gln Leu Leu
                 20                  25                  30

Ser Glu Pro Ser Pro Lys Ala Pro Arg Ala Arg Pro Cys Arg Val Ser
             35                  40                  45

Thr Ala Asp Arg Ser Val Arg Lys Gly Ile Met Ala Tyr Ser Leu Glu
 50                  55                  60

Asp Leu Leu Leu Lys Val Arg Asp Thr Leu Met Leu Ala Asp Lys Pro
 65                  70                  75                  80

Phe Phe Leu Val Leu Glu Glu Asp Gly Thr Thr Val Glu Thr Glu Glu
                 85                  90                  95

Tyr Phe Gln Ala Leu Ala Gly Asp Thr Val Phe Met Val Leu Gln Lys
            100                 105                 110

Gly Gln Lys Trp Gln Pro Pro Ser Glu Gln Gly Thr Arg His Pro Leu
        115                 120                 125

Ser Leu Ser His Lys Pro Ala Lys Lys Ile Asp Val Ala Arg Val Thr
    130                 135                 140

Phe Asp Leu Tyr Lys Leu Asn Pro Gln Asp Phe Ile Gly Cys Leu Asn
145                 150                 155                 160
```

```
Val Lys Ala Thr Phe Tyr Asp Thr Tyr Ser Leu Ser Tyr Asp Leu His
                165                 170                 175

Cys Cys Gly Ala Lys Arg Ile Met Lys Glu Ala Phe Arg Trp Ala Leu
            180                 185                 190

Phe Ser Met Gln Ala Thr Gly His Val Leu Leu Gly Thr Ser Cys Tyr
        195                 200                 205

Leu Gln Gln Leu Leu Asp Ala Thr Glu Glu Gly Gln Pro Pro Lys Gly
    210                 215                 220

Lys Ala Ser Ser Leu Ile Pro Thr Cys Leu Lys Ile Leu Gln
225                 230                 235
```

<210> SEQ ID NO 13
<211> LENGTH: 239
<212> TYPE: PRT
<213> ORGANISM: Mus sp.

<400> SEQUENCE: 13

```
Met Asp Tyr Ala Met Lys Ser Leu Ser Leu Leu Tyr Pro Arg Ser Leu
1               5                   10                  15

Ser Arg His Val Ala Val Ser Thr Ala Val Val Thr Gln Gln Leu Val
            20                  25                  30

Ser Lys Pro Ser Arg Glu Thr Pro Arg Ala Arg Pro Cys Arg Val Ser
        35                  40                  45

Thr Ala Asp Arg Lys Val Arg Lys Gly Ile Met Ala His Ser Leu Glu
    50                  55                  60

Asp Leu Leu Asn Lys Val Gln Asp Ile Leu Lys Leu Asp Lys Pro
65                  70                  75                  80

Phe Ser Leu Val Leu Glu Glu Asp Gly Thr Ile Val Glu Thr Glu Glu
                85                  90                  95

Tyr Phe Gln Ala Leu Ala Lys Asp Thr Met Phe Met Val Leu Leu Lys
            100                 105                 110

Gly Gln Lys Trp Lys Pro Pro Ser Glu Gln Arg Lys Lys Arg Ala Gln
        115                 120                 125

Leu Ala Leu Ser Gln Lys Pro Thr Lys Lys Ile Asp Val Ala Arg Val
    130                 135                 140

Thr Phe Asp Leu Tyr Lys Leu Asn Pro Gln Asp Phe Ile Gly Cys Leu
145                 150                 155                 160

Asn Val Lys Ala Thr Leu Tyr Asp Thr Tyr Ser Leu Ser Tyr Asp Leu
                165                 170                 175

His Cys Tyr Lys Ala Lys Arg Ile Val Lys Glu Met Leu Arg Trp Thr
            180                 185                 190

Leu Phe Ser Met Gln Ala Thr Gly His Met Leu Leu Gly Thr Ser Ser
        195                 200                 205

Tyr Met Gln Gln Phe Leu Asp Ala Thr Glu Glu Gly Pro Ala Lys
    210                 215                 220

Ala Lys Pro Ser Ser Leu Leu Pro Ala Cys Leu Lys Met Leu Gln
225                 230                 235
```

<210> SEQ ID NO 14
<211> LENGTH: 246
<212> TYPE: PRT
<213> ORGANISM: Macaca mulatta

<400> SEQUENCE: 14

```
Met Gly Ser Leu Arg Lys Gly Phe Gly Leu Leu Lys Asp Pro Trp Glu
1               5                   10                  15
```

```
Arg Ala Gly Phe Asp Trp Ala Ala Cys Leu Arg Val Ser Val Arg Thr
            20                  25                  30

Ser Val Val Thr Gln Gln Leu Leu Ser Glu Pro Ser Pro Glu Ala Pro
        35                  40                  45

Arg Ala Arg Pro Cys Arg Val Ser Thr Ala Asp Arg Ser Val Arg Lys
    50                  55                  60

Gly Ile Met Ala Tyr Ser Leu Glu Asp Leu Leu Leu Lys Val Arg Asp
65                  70                  75                  80

Thr Leu Met Leu Ala Asp Lys Pro Phe Phe Leu Val Leu Glu Glu Asp
                85                  90                  95

Gly Thr Thr Val Glu Thr Glu Glu Tyr Phe Gln Ala Leu Ala Gly Asp
            100                 105                 110

Ile Val Phe Met Val Leu Gln Lys Gly Gln Lys Trp Gln Pro Pro Ser
        115                 120                 125

Glu Gln Gly Thr Arg His Pro Gln Ser Leu Ser His Lys Pro Ala Lys
    130                 135                 140

Lys Ile Asp Val Ala Arg Val Thr Phe Asp Leu Tyr Lys Leu Asn Pro
145                 150                 155                 160

Gln Asp Phe Ile Gly Cys Leu Asn Val Lys Ala Thr Phe Tyr Asp Thr
                165                 170                 175

Tyr Ser Leu Ser Tyr Asp Leu His Cys Cys Gly Ala Lys Arg Ile Val
            180                 185                 190

Lys Glu Ala Leu Arg Trp Ala Leu Phe Ser Met Gln Ala Thr Gly His
        195                 200                 205

Val Met Leu Gly Thr Ser Cys Tyr Leu Gln Gln Leu Leu Asp Ala Thr
    210                 215                 220

Glu Gly Gln Pro Pro Lys Gly Lys Ala Ser Ser Leu Ile Pro Thr
225                 230                 235                 240

Cys Leu Arg Ile Leu Gln
                245

<210> SEQ ID NO 15
<211> LENGTH: 238
<212> TYPE: PRT
<213> ORGANISM: Canis familiaris

<400> SEQUENCE: 15

Met Glu Tyr Ala Met Lys Ser Leu Ser Leu Leu Tyr Pro Lys Ser Leu
1               5                   10                  15

Ser Arg His Val Ala Val Ser Thr Ser Val Val Thr Gln Gln Leu Ser
            20                  25                  30

Ser Lys Ser Ser Leu Glu Ala Pro Lys Ala Arg Pro Cys Arg Val Ser
        35                  40                  45

Thr Ala Asp Arg Ser Val Arg Lys Gly Ile Ile Ala His Ser Leu Lys
    50                  55                  60

Asp Leu Leu Asn Lys Val Arg Asp Thr Leu Leu Leu Ala Asp Lys Pro
65                  70                  75                  80

Phe Tyr Leu Val Leu Glu Glu Asp Gly Thr Thr Val Glu Thr Glu Glu
                85                  90                  95

Tyr Phe Gln Ala Leu Ala Asp Asp Thr Val Phe Met Val Leu Gln Lys
            100                 105                 110

Gly Gln Lys Trp Gln Pro Pro Gln Glu Gln Gly Ser Arg Tyr Gln Leu
        115                 120                 125

Ser Leu Ser His Lys Pro Ala Lys Lys Ile Asp Val Ala Gln Val Thr
    130                 135                 140
```

Phe Asp Leu Tyr Lys Met Asn Pro Gln Asp Phe Ile Gly Cys Leu Asn
145                 150                 155                 160

Val Lys Ala Thr Leu Tyr Gly Thr Tyr Ser Leu Ser Tyr Asp Leu His
            165                 170                 175

Cys Tyr Gly Ala Lys Arg Ile Met Lys Glu Val Leu Arg Trp Ala Leu
            180                 185                 190

Phe Ser Met Lys Thr Thr Gly His Val Leu Leu Gly Thr Ser Cys Tyr
            195                 200                 205

Met Gln Gln Leu Leu Asp Ala Thr Glu Gly Gly Gln Pro Pro Glu Gly
            210                 215                 220

Lys Ala Arg Ser Leu Ile Pro Thr Ser Leu Lys Met Leu Gln
225                 230                 235

<210> SEQ ID NO 16
<211> LENGTH: 222
<212> TYPE: PRT
<213> ORGANISM: Bos taurus

<400> SEQUENCE: 16

Met Ala Met Tyr Thr Ala Val Ser Thr Ser Val Val Thr Gln Gln Gln
1               5                   10                  15

Leu Ser Glu Pro Ser Ala Glu Ala Pro Arg Ala Arg Pro Cys Arg Val
            20                  25                  30

Thr Thr Ala Asp Arg Ser Val Arg Lys Gly Ile Met Val His Ser Leu
            35                  40                  45

Glu Asp Leu His Val Lys Val Gln Asp Thr Leu Met Leu Ala Tyr Arg
50                  55                  60

Pro Phe Phe Leu Val Leu Glu Glu Asp Gly Thr Thr Val Glu Thr Glu
65                  70                  75                  80

Glu Tyr Phe Gln Ser Leu Ala Asp Asp Thr Val Phe Met Val Leu His
            85                  90                  95

Lys Gly Gln Lys Trp Gln Pro Pro Ser Glu Gln Ser Thr Arg Tyr Gln
            100                 105                 110

Leu Ala Leu Ser His Lys Pro Ala Lys Ile Asp Val Ala Gln Val Thr
            115                 120                 125

Phe Asp Leu Tyr Lys Val Asn Pro Gln Asp Phe Ile Gly Cys Leu Asn
            130                 135                 140

Val Lys Ala Thr Leu Tyr Gly Thr Tyr Ser Val Ser Tyr Asp Leu His
145                 150                 155                 160

Cys Ser Gly Ala Lys Arg Ile Met Lys Glu Ala Leu Arg Trp Ala Leu
            165                 170                 175

Phe Ser Met Arg Thr Thr Gly His Met Leu Leu Gly Thr Ser Cys Tyr
            180                 185                 190

Leu Gln Gln Leu Leu Asp Ala Thr Glu Arg Glu Gln Pro Pro Lys Ser
            195                 200                 205

Lys Ala Ala Ser Leu Ile Pro Thr Ser Leu Lys Met Leu Gln
210                 215                 220

<210> SEQ ID NO 17
<211> LENGTH: 236
<212> TYPE: PRT
<213> ORGANISM: Xenopus sp.

<400> SEQUENCE: 17

Met Glu Tyr Ala Met Lys Ser Leu Ser Leu Leu Ser Pro Lys Ser Leu
1               5                   10                  15

-continued

```
Thr Lys Cys Val Ser Val Ser Ala Ser Met Thr Gln Gln Leu Leu Ser
            20              25              30

Arg Pro Val Ser Lys Pro Arg Pro Phe Arg Val Cys Asn Ser Asn Arg
            35              40              45

Ser Leu Arg Lys Gly Ile Val Ala Asn Ser Leu Glu Asp Leu Ile Asn
50              55              60

Lys Thr Gln Asp Ala Leu Leu Met Leu Glu Ala Ile Thr Leu Val Leu
65              70              75              80

Asp Glu Asp Gly Thr Cys Val Asp Thr Glu Glu Phe Phe Arg Ser Leu
                85              90              95

Asp Asp Gly Ala Val Phe Met Ala Leu Ala Lys Gly Gln Lys Trp Lys
            100             105             110

Pro Thr Glu Asn Ser Gly Tyr His Leu Ser Leu Thr Lys Lys Pro Ala
            115             120             125

Arg Lys Ile Asp Val Ala Cys Val Ser Phe Asp Leu Tyr Lys Asn His
    130             135             140

Pro Arg Asp Phe Ile Gly Cys Leu Asn Val Lys Ala Thr Leu Tyr Gly
145             150             155             160

Thr Tyr Ser Leu Ser Tyr Asp Leu Gln Cys Tyr Gly Ala Lys Arg Met
            165             170             175

Val Lys Glu Ala Leu Arg Trp Thr Leu Tyr Thr Met Gln Ala Thr Gly
            180             185             190

His Val Leu Leu Gly Thr Ser Cys Tyr Met Lys Gln Leu Leu Asp Ala
            195             200             205

Thr Glu Arg Pro Val Thr Glu Glu Lys Ser Ser Thr Thr Leu Arg
            210             215             220

Asp Phe Ile Pro Phe Ser Pro Trp Lys Met Leu Gln
225             230             235
```